United States Patent [19]

Sakamoto et al.

[11] Patent Number: 4,539,234

[45] Date of Patent: Sep. 3, 1985

[54] URETHRAL CATHETER CAPABLE OF PREVENTING URINARY TRACT INFECTION AND PROCESS FOR PRODUCING THE SAME

[75] Inventors: Izumi Sakamoto; Kunihiko Takagi, both of Kyoto, Japan

[73] Assignee: Unitika Ltd., Amagasaki, Japan

[21] Appl. No.: 382,743

[22] Filed: May 27, 1982

[30] Foreign Application Priority Data

May 27, 1981 [JP] Japan ................................ 56-81474
Nov. 13, 1981 [JP] Japan ................................ 56-182729

[51] Int. Cl.³ .......................... A61M 25/00; B05D 3/02
[52] U.S. Cl. .................................. 427/393.5; 604/265; 521/25; 521/28
[58] Field of Search ................ 604/265; 521/32, 33; 427/393.5; 521/25, 28, 38

[56] References Cited

U.S. PATENT DOCUMENTS

| | | | |
|---|---|---|---|
| 3,226,380 | 12/1965 | Knight | 521/25 |
| 3,311,608 | 3/1967 | Murphy | 521/25 |
| 4,058,491 | 11/1977 | Steckler | 521/32 X |
| 4,107,121 | 8/1978 | Stoy | 524/391 |
| 4,109,080 | 8/1978 | Lieser et al. | 521/25 |
| 4,228,205 | 10/1980 | Hudecek et al. | 521/28 |
| 4,248,992 | 2/1981 | Takago | 521/28 |
| 4,453,991 | 6/1984 | Grot | 521/28 |

FOREIGN PATENT DOCUMENTS 97295  8/1976  Japan .................................. 604/265

Primary Examiner—John E. Kittle
Assistant Examiner—James J. Seidleck
Attorney, Agent, or Firm—Sughrue, Mion, Zinn, Macpeak, and Seas

[57] ABSTRACT

A urethral catheter composed of olefin polymer, diene polymer or silicone polymer as a base material wherein an antimicrobial substance being chemically bonded with the inside wall and/or the outside wall thereof, and a process for producing the same. This urethral catheter effectively prevents urinary tract infection for a long period of time.

7 Claims, No Drawings

URETHRAL CATHETER CAPABLE OF PREVENTING URINARY TRACT INFECTION AND PROCESS FOR PRODUCING THE SAME

FIELD OF THE INVENTION

The present invention relates to a urethral catheter capable of preventing urinary tract infection and a process for producing the same.

BACKGROUND OF THE INVENTION

In many cases of spinal injury, cerebral hemorrhage and softening of the brain, after an operation the patient develops symptoms such as dysuria or urinary incontinence. In such cases, urethral catheterization using a catheter is adopted in order to secure a smooth urinary passage. This is done in order to maintain kidney functions or prevent or promote the leakage of urine. The catheters used in such cases are called urethral catheters. Such catheters must have sufficient flexibility, elasticity and innoxious property because of their use. Almost all of them are composed of a material such as an olefin polymer, diene polymer or silicone polymer as the base material.

Since catheterization is a remarkably useful curative means for carrying out rapid urination, it is frequently used in fields other than urology such as surgery, internal medicine and obstetrics and gynecology. However, the procedure is defective in that the occurrence of infection is nearly unavoidable if the urethral catheter is inserted into the urinary tract. Since the urethral catheter is left in the urinary tract for a long time, microbes intrude into the urinary tract through the catheter frequently causing symptoms such as urethritis, cystitis or pyelitis. It has been reported that performing an opening continuation catheterization which is frequently used hitherto (a method of collecting urine in a container such as a glass bottle which is not sterilized), infection occurs within 3 days in 42 to 80% of the clinical test and the infection is observed in all cases after the 7th day.

Therefore, with respect to prevention of urinary tract infection, methods such as washing of the bladder or injection of antiseptics or disinfectants are utilized. However, such procedures are disadvantageous because the operation is troublesome and the operation itself becomes a new source of infection.

Further, chemotherapy such as preventive administration of antibiotics, etc. has been carried out. However, it is said that chemotherapy is sometimes even rather harmful due to problems in the administration of large amounts or, even a small amount of antibiotics depending upon the kind of antibiotics. The administration frequently causes an ill effect and a microbe-exchange phenomenon may easily appear if an infection is caused. Thus, topical utilization is generally more desirable for antibiotics.

With respect to topical utilization of antibiotics, a method has been proposed which comprises applying an ointment containing antibiotics to a urethral catheter and a method which comprises coating the wall of the catheter with a resin to form a coating layer in which antibiotics are contained (Japanese Patent Publication 27680/79). However, in these cases, the catheter cannot be satisfactorily used, because the antibiotics flow outside the body within a very short time by urine after insertion of the catheter, whereby the antimicrobial function cannot be observed within a short time, because the antibiotics are merely adsorbed on the supporting layer.

Another method involves directly dropping a diluted solution of antibiotics into the bladder using a so-called three-way catheter. This method is only utilized in some areas of urology and it cannot be used in other clinical fields under existing circumstances, because handling is difficult and troublesome.

Intrusion passages of microbes include: (1) counter-current intrusion through a space between the urethral catheter and a mucous membrane of the urinary tract (outside tract passage), (2) intrusion through a bonding part of the urethral catheter and a conduit (including treatments such as washing, etc.), and (3) counter-current intrusion in the interior of the conduit and the urethral catheter from a urine collecting part (inside tract passage). In case of intrusion by the outside tract passage, microbes which are usually present in the urethra rapidly intrude upwards along the wall of the urethral catheter in the early stage of insertion of the catheter and reach the neck part of the bladder. For such infection, the antibiotics which are present on the wall of the urethral catheter exhibit their antimicrobial function, because they can directly touch the microbes. However, microbes intruding through the inside tract passage, for example, microbes intruding from a urine collecting means, namely, microbes dropping or intruding in the urine collecting means, multiply in the urine collected and reach the bladder with back flow urine or rising bubbles. In fact, in an experiment under a static state, it has been ascertained that microbes go backwards in urine in a manner similar to carp ascending a waterfall. Since antibiotics are present on the wall of the urethral catheter, they cannot directly touch microbes intruding from such a passage, and there is the possibility that microbes which are not affected by the antimicrobial function will remain. Therefore, sufficient ability to prevent infection has not been obtained. In order to prevent infection from all intrusion passages, it is necessary for the antibiotics to be present on the wall of urethral catheter and also be gradually released from the wall of the catheter to diffuse into urine so that they contact microbes ascending and wafting in the urine. Therefore, the rate of which microbes separate from the wall is important. As described above, when a method which comprises applying antibiotics or an ointment containing antibiotics to the catheter or a method which comprises coating the wall of the catheter with a resin containing antibiotics is used, the antibiotics easily flow outside the body with the flow of urine. Accordingly, within a short period of time, both the wall and the urine do not contain the antibiotics. Therefore, the ability to prevent infection is completely eliminated within a very short period after insertion. In order to prevent infection, it is important to keep the concentration of antibiotics in the urine at an effective value or more for a long period of time by controlling the rate of antibiotics released from the wall. However, urethral catheter having this ability are as yet unknown.

SUMMARY OF THE INVENTION

An object of the present invention is to provide a urethral catheter, particularly indwelling urethral catheter which can be simply used and which can prevent infection from all intrusion passages for a long period of time without becoming a new source of infection itself.

As a result of various studies to attain the above described object, it has been found that, when an antimicrobial substance is chemically bonded with the inside wall or the outside wall of a urethral catheter composed of olefin polymer, diene polymer or silicone polymer as a base material, the antimicrobial substance is gradually separated from the wall at a desired rate into urine to diffuse therein without flowing outside the body by urine within a short period of time, when the urethral catheter is inserted into the body. Therefore, antimicrobial substances are maintained at an effective concentration in the urine for a long period of time. Thus, the present invention has been completed.

The present invention relates to a urethral catheter capable of preventing urinary tract infection which comprises a urethral catheter comprised of a material selected from the group consisting of an olefin polymer, a diene polymer or a silicone polymer as the base material, and an antimicrobial substance being chemically bonded with the inside and/or outside walls of the urethral catheter; and a process for producing the urethral catheter which comprises bonding chemically an antimicrobial substance with the inside wall and/or the outside wall of the urethral catheter.

DETAILED DESCRIPTION OF THE INVENTION

The term olefin polymer was used in the present invention means polymers prepared by homopolymerization or copolymerization of hydrocarbons having one double bond, such as ethylene, propylene, 1-butene, 3-methyl-1-butene, 3,3-dimethyl-1-butene, 1-pentene, 4-methyl-1-pentene, 3-methyl-1-pentene, 1-hexene, 4-methyl-1-hexene, 5-methyl-1-hexene, 1-heptene, 1-octene, 1-decene, 1-hexadecene, 1-octadecene, vinyl cyclopropane, vinyl cyclohexane, isobutylene, 2-methyl-1-pentene, cyclobutene or norbornene by a known process.

The term diene polymer as used in the present invention means polymers prepared by homopolymerization or copolymerization of hydrocarbons having two double bonds such as butadiene, isoprene, 1,3-pentadiene, 1,5-hexadiene or 1,6-heptadiene by a known process. By way of exception, cis-1,4-polymer of isoprene which generally exists as natural rubber is suitably used in the present invention.

Examples of other copolymerizable components include vinyl acetate, methyl vinyl ether, styrene, vinyl chloride, vinylidene chloride, maleic acid anhydride, acrylic acid, methacrylic acid, acrylonitrile, methyl methacrylate, sulfur dioxide, vinylpyridine, chloroprene, ethylene oxide and formaldehyde.

Examples of the silicone polymer used in the present invention include dimethyl polysiloxane, methylphenyl polysiloxane, cyanoalkylmethyl polysiloxane and fluoroalkylmethyl siloxane. Among them, dimethyl polysiloxane is particularly preferred in view of its high elasticity, high strength and innoxious property.

The term antimicrobial substance as used in the present invention means antibiotics, antiseptics and disinfectants. Examples of antibiotics include erythromycin ethyl succinate, erythromycin ethylcarbonate, erythromycin glucoheptanoate, erythromycin stearate, erythromycin lauryl sulfate propionate, erythromycin lactobionate, triacetyl oleandomycin, oleandomycin phosphate, amikacin sulfate, bekanamycin sulfate, aminodeoxykanamycin, kanamycin monosulfate, tobramycin, acetyl kitasamycin, kitasamycin, kitasamycin succinate, kitasamycin tartarate, chloramphenicol, chloramphenicol alginine succinate, chloramphenicol sodium succinate, chloramphenicol stearate, chloramphenicol morpholinoacetate, chloramphenicol palmitate, chloramphenicol stearoylglycolate, chloramphenicol sulfate morpholinoacetate, colistin hydrochloride, colistin, colistin sodium methane sulfonate, colistin sulfate, josamycin, josamycin propionate, dihydrostreptomycin hydrochloride, dihydrostreptomycin sulfate, compound streptomycin, streptomycin hydrochloride, streptomycin calcium chloride hydrochloride, streptomycin sulfate, streptomycin isoniazone sulfate, cephacetrile sodium, cephazolin sodium, cephapyrin sodium, cephalexin, cephaglycin, cephalothin sodium, cephaloridine, ceftezol sodium, cephradine, oxytetracycline hydrochloride, oxytetracycline, oxytetracycline calcium, chlorotetracycline hydrochloride, chlorotetracycline, tetracycline hydrochloride, rolitetracycline nitrate, tetracycline L-methylene-lysine, tetracycline methaphosphate, rolitetracycline, dimethylchlorotetracycline hydrochloride, dimethylchlorotetracycline, doxycycline hydrochloride, minocycline hydrochloride, metacycline hydrochloride, actinomycin D, azalomycin F, amphotericin B, enbiomycin sulfate, enramycin hydrochloride, aureothricin, capreomycin sulfate, carzinophilin, carbomycin, gramicidin, gramicidine S hydrochloride, griseofulvin, chromomycin A3, gentamycin sulfate, cycloserin, sarkomycin, siccanin, dibekacin sulfate, acetylspiramycin, spiramycin, spectinomycin hydrochloride, daunorubicin hydrochloride, doxorubicin hydrochloride, trichomycin, nystatin, neocarzinostatin, novobiocin calcium, novobiocin sodium, viomycin sulfate, bacitracin, variotin, paromomycin sulfate, pimaricin, pyrrolnitrin, fusidate sodium, fradiomycin palmitate, fradiomycin sulfate, bleomycin hydrochloride, bleomycin sulfate, ampicillin, ampicillin sodium, talampicillin hydrochloride, carbenicillin sodium, carbenicillin indanyl sodium, carbenicillin phenyl sodium, phenoxymethylpenicillin, phenoxymethylpenicillin potassium, phenoxymethylpenicillin calcium, phenoxymethylpenicillin benzathine, penicillin potassium, penicillin sodium, penicillin procaine, benzylpenicillin potassium, benzylpenicillin sodium, benzylpenicillin procaine, benzylpenicillin benzathine, compound penicillin potassium, compound benzylpenicillin potassium, compound benzylpenicillin sodium, compound benzylpenicillin benzathine, clindamycin hydrochloride, clindamycin palmitate hydrochloride, lincomycin hydrochloride, amoxicillin, oxacillin sodium, cloxacillin sodium, cyclacillin, dicloxacillin sodium, sulbenicillin sodium, pivmecillinam hydrochloride, phenethicillin potassium, flucloxacillin sodium, propicillin potassium, hetacillin potassium, methicillin sodium, pentamycin, polymyxin B sulfate, mitomycin C, maridomycin propionate, mikamycin, midecamycin, rifampicin, ribostamycin sulfate, pyrrolenitrin, actinomycin, bleomycin, daunorubicin, doxorubicin and neocarzinostatin. Aminoglucosides and polymyxins are preferred to use, because they have strong alkalinity and a high antibiotic action to microbes which cause urinary tract infection. As the antiseptics and disinfectants, it is preferred to use dyestuff medical preparations such as acrinol or acriflavine, etc., furan medical preparations such as nitrofurazone, etc., cationic soap medical preparations such as benzalkonium chloride or benzethonium chloride, etc., cyclohexidine and povidone-iodine.

These antimicrobial substances can be used alone or as a combination of two or more of them, and they are chemically bonded with the inside wall or the outside wall of the urethral catheter.

The urethral catheter of the present invention can be prepared by the following processes.

(A) Ion-exchange groups are chemically introduced into the molecules of the inside wall and/or the outside wall of the urethral catheter and, subsequently, the introduced ion-exchange groups are ionically bonded with an antimicrobial substance.

(B) Functional groups capable of easily converting into ion-exchange groups by hydrolysis are chemically introduced into the molecules of the inside wall and/or the outside wall of the urethral catheter and subsequently the ion-exchange groups obtained by hydrolyzing the introduced functional groups are ionically bonded with the antimicrobial substance.

(C) The inside wall and/or the outside wall of the urethral catheter is coated with a compound having ion-exchange groups and subsequently ion-exchange groups in the coating layer are ionically bonded with the antimicrobial substance.

(D) The inside wall and/or the outside wall of the urethral catheter was coated with a compound having functional groups capable of easily converting into ion-exchange groups by hydrolysis and subsequently ion-exchange groups obtained by hydrolyzing the functional groups in the coating layer are ionically bonded with the antimicrobial substance.

(E) Two or more compounds are subjected to reacting on the inside wall and/or the outside wall of the urethral catheter to form a film having an ion-exchange group on the inside wall and/or the outside wall and, subsequently, the ion-exchange groups are ionically bonded with the antimicrobial substance.

(F) Two or more compounds are subjected to reacting on the inside wall and/or the outside wall of the urethral catheter to form a film having functional groups capable of easily converting into ion-exchange groups by hydrolysis and, subsequently, ion-exchange groups obtained by hydrolyzing the functional groups in the film are ionically bonded with the antimicrobial substance.

In these processes (A) to (F), the processes (E) and (F) are preferred and the process (F) is more preferred.

According to these processes, since the antimicrobial substance is held on the inside wall or the outside wall of the urethral catheter by an ionic bond, it does not flow out of the body with the urine in a short period of time like an antimicrobial substance supported by mere physical adsorption or coating. The ionic bond gradually dissociates and, consequently, the antimicrobial substance gradually diffuses into the urine keeping the concentration of the antimicrobial substance in the urine at a minimum inhibitory concentration (MIC), namely, a minimum concentration necessary to kill microbes in the urine, for a long period of time. The minimum inhibitory concentration (MIC) cannot be absolutely specified because it is determined by the amount of a specific antimicrobial substance to be needed to kill a specific microbes. However, 0.1 to 15 $\mu$g/ml (the factor of the antimicrobial substance/the volume of urine) is generally preferred as a MIC in many cases.

Examples of the above described ion exchange groups include an amino group, carboxyl group and a sulfonic acid group, preferably a carboxyl group. Examples of the functional groups capable of easily converting into ion-exchange groups in the present invention include acid anhydride groups and sulfonic acid chloride group which are easily converted into a carboxyl group or a sulfonic acid group by reacting with water at a room temperature or so, preferably acid anhydride groups.

In the above described processes (A) and (B), for example, the following reactions (i) to (vi) can be adopted as reactions for chemically introducing ion-exchange groups or functional groups capable of easily converting into ion-exchange groups into the polymer. Reactions (i) to (iv) are utilized for olefin polymers, reactions (i) and (v) are utilized for diene polymers and reaction (vi) is utilized for silicone polymers. The reaction for introduction may be carried out prior to molding of the urethral catheter or may be carried out after molding of the urethral catheter, preferably after molding of the urethral catheter.

(i) A vinyl monomer having reactive functional groups such as acrylic acid, methacrylic acid or maleic acid anhydride is copolymerized with an olefine or diene to introduce carboxyl groups or acid anhydride groups (J. De Merlier and J. Le Bras: Industrial and Engineering Chemistry; Product Research and Development; Vol. 2, page 22, (1963)), (U.S. Pat. No. 3,177,269 incorporated herein by reference).

(ii) A plasma processing is carried out in the presence of ammonia or a mixed gas composed of nitrogen and hydrogen to introduce amino groups (J. R. Hollahan, B. B. Stafford, R. D. Falb and S. T. Payne: Journal of Polymer Science; Vol. 13, page 807, (1969)).

(iii) A surface treatment is carried out with fuming nitric acid to introduce sulfonic acid groups (Shin Ogawara: Kobunshi no Kagakuhanno; Vol. 1, page 12, published by Kagakudojin Co.).

(iv) It is previously activated with ozone and processed with a $C_3O_2$ solution to introduce carboxylic acid groups (Shin Ogawara: Kobunshi no Kagakuhanno; Vol. 1, page 14, published by Kagakudojin Co.).

(v) Nitrile oxide prepared using benzhydroxamil chloride is reacted with double bond (C═C) to introduce the carboxyl group (Shin Ogawara: Kobunshi no Kagakuhanno; Vol. 1, page 22, published by Kagakudojin Co.).

(vi) It is allowed to react with a silane coupling agent such as n-$\beta$-(aminoethyl)-$\gamma$-aminopropyl trimethoxy silane or n-$\beta$-(aminoethyl)-$\gamma$-aminopropyl methyldimethoxy silane, etc. to introduce amino groups. This reaction is carried out, for example, by processing with a 10 wt% solution of $\gamma$-aminopropyltriethoxy silane in chloroform at a room temperature for 24 hours or so.

Examples of compounds used for coating in the above described processes (C) and (D) include the following compounds: Polycarboxylic acids such as polyacrylic acid, polymethacrylic acid, polymaleic acid, poly-(maleic acid monoester), polyaspartic acid, polyglutamic acid, alginic acid or pectinic acid, polycarboxylic acid anhydrides such as polymaleic anhydride, polymethacrylic anhydride or polyacrylic acid anhydride, polyamines and polyammonium ions such as polyethylene imine, polyvinylamine, polylysine, poly-(dialkylaminoethyl methacrylate), poly-(dialkylaminomethyl styrene), poly-(vinylpyridine), poly-(2-methacryloxyethyl trialkyl ammonium ion), poly-(vinylbenzyl trialkyl ammonium ion), poly-(N,N-dialkyl-3,5-methylenepiperidinium ion), poly-(vinyl-N-alkylpyridinium ion) or poly-(dialkyloctamethylene ammonium ion), and polysulfonates such as poly-(vinyl sulfonate) or poly-(styrene sulfonate).

Linear copolymers, crosslinked copolymers, graft copolymers and block copolymers containing the monomers as constituents of the above exemplified polymers can also be used in and are included within the scope of the present invention. A suitable molecular weight for these polymeric materials will depend on the mechanical strength desired for the coating, but generally is more than about 500, preferably more than 10,000.

In the above described processes (C) and (D), the above described compound for coating is used by dissolving in a suitable solvent or the compound per se is used when it is liquid itself, and it is applied by a known method such as a dip coating method, a spray coating method or a brush coating method, etc. In carrying out the coating, the compound for coating may be used alone or may be used as a mixture of two or more of them. Formation of a plurality of coating layers is carried out, for example, as follows. More specifically, when it is necessary to bond a large amount of an antimicrobial substance having only anion-exchange groups to a urethral catheter into which only carboxyl groups are introduced in an insufficient amount, a compound having amino groups in a large amount, such as polyethylene imine, is previously applied to form a coating layer and a compound having carboxylic acid anhydride groups in an excess amount, such as maleic anhydride copolymer, is applied to the resulted coating layer. Then, the reactive functional groups are ionized to obtain cation-exchange groups, by which ionic bonds are formed between the cation-exchange groups and the anion-exchange groups in the antimicrobial substance. Further, if necessary, it is desirable to provide an adhesive layer or admix an adhesive with the compound for coating according to the kind of compound for coating or raw material for the urethral catheter.

As the solvent used for coating, any material may be used if it dissolves the compound for coating and does not erode the base material of the urethral catheter. However, the present invention have found it useful for carrying out effective coating to use a solvent which swells the base material of the urethral catheter at coating but does not damage the strength and dimensional stability of the base material after evaporation of the solvent (for example, solvent mixture composed of tetrahydrofuran and water for natural rubber).

The reaction of two or more compounds in the above described processes (E) and (F) can be carried out, for example, by the following processes (1) to (10).

(1) A process which comprises reacting (A) a compound having amino groups with (B) a polyfunctional compound having a plurality of groups selected from an aldehyde group, an isocyanate group, a thioisocyanate group, an epoxy group, a carboxyl group and a sulfonic acid group under a condition of an excess amount of the compound having amino groups (A).

(2) A process which comprises reacting (A) a compound having amino groups with (B) a polyfunctional compound having a plurality of carboxyl group under a condition of an excess amount of the polyfunctional compound having a plurality of carboxyl group (B).

(3) A process which comprises reacting (A) a compound having amino groups with (B) a polyfunctional compound having a plurality of sulfonic acid chloride group under a condition of an excess amount of the polyfunctional compound having a plurality of sulfonic acid chloride group (B) and thereafter hydrolyzing the sulfonic acid chloride groups.

(4) A process which comprises reacting (A) a compound having hydroxyl groups with (B) a polyfunctional compound having a plurality of isocyanate groups and thereafter hydrolyzing the isocyanate groups.

(5) A process which comprises reacting (A) a compound having hydroxyl groups with (B) a polyfunctional compound having a plurality of acid chloride groups and thereafter hydrolyzing the acid chloride groups.

(6) A process which comprises reacting (A) a compound having acid anhydride groups with (B) a polyfunctional compound having a plurality of amino groups under a condition of an excess amount of the polyfunctional compound having a plurality of amino groups (B).

(7) A process which comprises reacting (A) a compound having acid anhydride groups with (B) a polyfunctional compound having a plurality of amino groups.

(8) A process which comprises reacting (A) a compound having acid anhydride groups with (B) a polyfunctional compound having a plurality of amino groups under a condition of an excess amount of the compound having acid anhydride groups (A), and thereafter hydrolyzing the acid anhydride groups.

(9) A process which comprises reacting (A) a compound having acid anhydride groups with (B) a polyfunctional compound having a plurality of hydroxyl groups.

(10) A process which comprises reacting (A) a compound having acid anhydride groups with (B) a polyfunctional compound having a plurality of hydroxyl groups under a condition of an excess amount of the compound having acid anhydride groups (A), and thereafter hydrolyzing the acid anhydride groups.

Examples of the compounds having amino groups used in the above described processes (1), (2) and (3) include the following compounds: Polyvinylamine, polylysine, poly(dialkylaminoethyl methacrylate), poly-(dialkylaminomethylstyrene), polyamine synthesized from amine and alkylene dihalide or epichlorohydrin (Encyclopedia of Poly Science and Technology, Vol. 10, page 10) and alkyleneimine polymers obtained by ring opening polymerization of ethyleneimine or propyleneimine, etc. (Encyclopedia of Polymer Science and Technology; Vol. 1, page 734). Among the above described compounds, polyethyleneimine is particularly preferred because it is cheap and has a number of amino groups.

Examples of the compounds having hydroxyl groups used for the above described reactions (4) and (5) include esterified derivatives of cellulose such as acetyl cellulose, cellulose propionate, cellulose butylate, nitrocellulose, cellulose acetate, cellulose phosphate or cellulose dithiocarboxylate, etc., etherified derivatives of cellulose such as methyl cellulose, ethyl cellulose, benzyl cellulose, trimethyl cellulose, cyanoethyl cellulose aminoethyl cellulose or oxyethyl cellulose, etc., polyvinyl alcohol, copolymers of polyvinyl alcohol and ethylene, propylene, vinyl chloride, allyl alcohol or N-vinyl pyrrolidone, etc., polyvinyl alcohol ether derivatives such as methyl, ethyl, propyl, butyl, octyl, dodecyl or phenyl ether of polyvinyl alcohol, polyvinyl alcohol acetal derivatives such as formal, ethylal, butyral or aminoacetal, etc. of polyvinyl alcohol, polyvinyl alcohol ester derivatives such as acetate, formate, butyrate, caproate, laurate, stearate or benzoate, etc. of polyvinyl alcohol, polyether polyol such as polyethylene glycol, polypropylene glycol, polytetramethylene glycol or polyethylene-polypropylene glycol, etc., polyesters having hydroxyl groups on both ends prepared by condensing dicarboxylic acid such as succinic acid, glutaric acid, adipic acid, sebacic acid, isophthalic acid, phthalic acid or terephthalic acid, etc. with glycol such as ethylene glycol, propylene glycol or butylene glycol, etc., and natural high molecular substances such as starch, gelatine or dextran.

Examples of the compounds having acid anhydride groups used for the above described reactions (6), (7), (8), (9) and (10) include polycarboxylic acid anhydrides such as, polymaleic acid anhydride, polyitaconic acid anhydride, polyacrylic acid anhydride or polymethacrylic acid anhydride, etc., preferably polymaleic acid anhydride, and copolymers comprising the above described polycarboxylic acid anhydride as a constitutional unit. For example, it is possible to use copolymers of maleic acid anhydride and aliphatic vinyl ether such as maleic acid anhydride-butanediol divinyl ether copolymer, maleic acid anhydride-ethyl vinyl ether copolymer, or maleic acid anhydride-methyl vinyl ether copolymer, etc., copolymers of maleic acid anhydride and olefin monomer such as maleic acid anhydride-ethylene copolymer or maleic acid anhydride-propylene copolymer, etc., copolymers of maleic acid anhydride and aromatic vinyl monomer such as maleic acid anhydride-styrene copolymer, etc., and copolymers of maleic acid anhydride and aliphatic vinyl ester such as maleic acid anhydride-vinyl acetate copolymer, etc.

In the polyfunctional compounds used for the above described processes (1) to (10), examples of polyfunctional compounds having aldehyde groups include glutaraldehyde, terephthalaldehyde, isophthalaldehyde and dialdehyde starch. Examples of the polyfunctional compounds having isocyanate groups include hexamethylene diisocyanate, toluene diisocyanate, xylene diisocyanate, phenylene diisocyanate and isocyanate derivatives of aniline-formaldehyde resin. An example of a polyfunctional compound having thioisocyanate groups is hexamethylene thioisocyanate. Examples of polyfunctional compounds having carboxyl groups include polycarboxylic acids such as alginic acid, pectinic acid or carboxymethyl cellulose, etc., homopolymers and copolymers of methacrylic acid, acrylic acid, maleic acid, itaconic acid, aspartic acid or glutamic acid, etc., alkyl esters of the above described acids such as methyl, ethyl propyl, butyl, amyl, hexyl, octyl or dodecyl ester, haloalkyl esters thereof such as chloromethyl, 2-chloroethyl or 2-bromoethyl ester, ether group containing esters thereof such as 2-ethoxyethyl, 2-butoxyethyl, 2-(2-ethoxymethoxy)ethyl or phenoxyethyl ester, basic nitrogen containing esters thereof such as 2-aminoethyl, 2-N,N'-dimethylaminoethyl or 2-N,N'-dipropylaminoethyl ester, mono- and diesters thereof such as ethylene glycol, diethylene glycol or triethylene glycol mono- or diester, etc. Examples of polyfunctional compounds having sulfonic acid chloride groups include sulfonic acid chlorides of polyethylene and polypropylene, etc.

Examples of polyfunctional compounds having acid chloride groups include polyacid chlorides such as adipoyl chloride, isophthaloyl chloride, terephthaloyl chloride or cyanuric chloride, etc.

Examples of polyfunctional compounds having amino groups include all of the above described compounds having amino groups used for the process (3). In addition, examples of low molecular polyamines include ethylenediamine, trimethylenediamine, 1,2-diaminopropane, 2-diaminopropane, tetramethylenediamine, 1,3-diaminobutane, 2,3-diaminobutane, pentamethylenediamine, 2,4-diaminopentane, hexamethylenediamine, octamethylenediamine, nonamethylenediamine, decamethylenediamine, undecamethylenediamine, dodecamethylenediamine, tridecamethylenediamine, octadecamethylenediamine, N,N-dimethylethylenediamine, N,N-diethyltrimethylenediamine, N,N-dimethyltrimethylenediamine, N,N-dibutyltrimethylenediamine, N,N,N'-triethylethylenediamine, N-methyltrimethylenediamine, N,N-dimethyl-p-phenylenediamine, N,N-dimethylhexamethylenediamine, diethylenetriamine, triethylenetetramine, tetraethylenepentamine, heptaethyleneoctamine, nonaethylenedecamine, 1,3-bis-(2'-aminoethylamino)propane, bis-(3-aminopropyl)amine, 1,3-bis-(3'-aminopropylamino)propane, 1,2,3-triaminopropane, tris-(2-aminoethyl)amine, tetra-(aminomethyl)methane, methyliminobispropylamine, methyliminobisethylamine, ethyliminobisethylamine, N-aminopropyl-2-morpholine, N-aminopropyl-2-pipecoline, N-(2-hydroxyethyl)-trimethylenediamine, xylylenediamine, phenylenediamine, piperazine, N-methylpiperazine, N-(2-aminoethyl)ethanolamine, N-aminoethylpiperazine, N,N,N',N'-tetramethylethylenediamine and N,N,N',N'-tetramethyltetramethylenediamine, etc.

Examples of polyfunctional compounds having a plurality of hydroxyl group used for the above described processes (9) and (10) include all of the exemplified compounds having hydroxyl groups used for the processes (4) and (5). In addition, examples of low molecular polyols include ethylene glycol, propylene glycol, butylene glycol, diethylene glycol, cyclohexanediol, pentaerythritol, glycerin and 1,1,1-trimethylolpropane, etc.

In order to produce the urethral catheter according to process (E) or (F) of the present invention, it is necessary to form a film on the inside or outside wall of the catheter by reacting the component (A) with the component (B) as described in the processes (1) to (10) on the inside wall or the outside wall. For this purpose, a solution prepared by mixing the component (A) and the component (B) using water or an organic solvent as a medium is brought into contact with the inside wall or the outside wall of the catheter and the catheter is then heated. Blending of both components can be carried out by any method, for example, a method which comprises blending a solution of the component (A) with a solution of the component (B) or a method which comprises adding a solvent to a mixture of component (A) and component (B). In order to enhance the blending effect to shorten the blending time, it is desired, if necessary, to heat or stir the mixture. Examples of organic solvents which can be used include ketones such as acetone or methyl ethyl ketone, etc., aldehydes such as benzaldehyde, formaldehyde or dimethylformaldehyde, etc., ethers such as tetrahydrofuran, etc., esters such as methyl acetate or ethyl acetate, etc., and alcohols such as methanol, ethanol, propanol, isopropanol or butanol, etc. However, it is necessary to select a solvent which does not react with the component (A) or the component (B) to be used. Ketones and alcohols are preferably used. These organic solvents may be used alone or may be used as a mixture of them as occasion demands. There are advantages to using the solvents as a mixture. For example, the mixture can be expected to carry out uniform dissolution or blending of component (A) and component (B) and to increase the adhesive strength of the film to the wall of the catheter. In order to bring the resulting solution into contact with the inside wall or the outside wall of the catheter, for example, the catheter is dipped into the solution, or the solution is sprayed on the catheter, or the solution is circulated into the catheter, or the solution is applied to the catheter by means of, for example, a doctor blade or a brush, etc. These methods can be suitably selected. After the solution is brought into contact with the catheter, the solvent is removed by drying. The catheter is then heated at, preferably, 30° to 180° C. and more preferably 50° to 160° C. for, preferably, 5 minutes to 48 hours and more preferably 10 minutes to 24 hours to react the component (A) with the component (B). This causes the film to be formed on the inside wall or the outside wall of the catheter.

In this process, if necessary, it is possible to bond the film composed of a reaction product of the component (A) and the component (B) to the catheter using an adhesive based on the type of components (A) and (B) used or the base material of the urethreal catheter, etc. In order to carry out adhesion, it is possible to adopt a process which comprises providing previously an adhesive layer on the inside wall or the outside wall of the catheter and carrying out the reaction of both components on the surface of the adhesive layer. Another process comprises adding previously an adhesive to the mixture of both components. The process which comprises providing the adhesive layer can be carried out according to the process for forming the above described film. In this case, it is possible to adopt a process which comprises using two or more adhesives as a mixture or by lamination and a process which comprises using two or more organic solvents. By utilizing such processes, firm adhesion of the wall of the catheter to the film can be obtained in many cases.

In order to bond the antimicrobial substance by an ionic bond in the above described processes (A) to (F), a process can be used which comprises spraying the solution with an antimicrobial substance. Another process comprises circulating the solution of the antimicrobial substance through the interior of the urethral catheter. The simplest process comprises dipping the urethral catheter in the solution of the antimicrobial substance. Generally, in order to carry out formation of the ionic bond effectively, it is preferred to carry out the processing at $-10°$ to 60° C., preferably 0° to 50° C., for several seconds to 72 hours, preferably 5 minutes to 48 hours. However, there are instances where the processing time is made longer according to the kind of the antimicrobial substance used and the form of the catheter used. In this case, the processing time is preferably about 2 to 10 days. Further, it is preferred to control the pH of the solution of the antimicrobial at a suitable range. For example, effective formation of the ionic bond is accomplished by carrying out the process while keeping the solution of antimicrobial substance at an alkaline state when using an antimicrobial substance having anion-exchange groups and at an acid state when using an antimicrobial substance having cation-exchange groups. This treatment is carried out by continuously adding dropwise acid or alkali during the progress of ionic bond reaction.

The catheters prepared by the above described processes (A) to (F) are very capable of preventing infection regardless of the process for production thereof.

Urethral catheters prepared by the processes (E) and (F) have particularly ideal characteristics with respect to preventing urinary tract infection. Namely, the urethral catheter remains in the body for 3 to 5 days in many cases, and sometimes 2 weeks or so and seldom 5 weeks or so. The urethral catheters produced by these processes have an ideal characteristic because they release gradually the antimicrobial substance over such a long period of time. They are also ideal with respect to the amount of the substance released. More specifically, a larger amount of antimicrobial substance is released during a period of 5 days after insertion of the catheter, namely, during a period having a particularly high infection ratio due to microbes subsisting in the urethra at ordinary times which are introduced into the bladder together with the catheter. After this period, the amount of releasing decreases gradually but the antimicrobial substance is released in an amount sufficient to prevent urinary tract infection even after 5 weeks. This characteristic of gradually decreasing the amount of releasing is not always necessary in the viewpoint of urinary tract infection. However, it is still advantageous from an economical point because it is not necessary to use a greater amount of antimicrobial substance than that required. It is also a desirable characteristic because there is less possibility of reducing the ability of preventing infection which is caused by the appearance of resistant microbes brought about by a continuous dosage of a large amount of antibiotics. Such characteristics are ideal ones for the urethral catheter.

As described above, the urethral catheters produced by the above processes (E) and (F) have particularly ideal characteristics with respect to preventing urinary tract infection. Among the above described processes (E) and (F), a particularly preferred process comprises reacting about 0.5 to about 99.5 parts by weight of (I) a copolymer of maleic acid anhydride and a copolymerizable aromatic vinyl monomer or olefin monomer (refer to component (I), hereinafter) and about 0.5 to about 99.5 parts by weight of (II) a copolymer of maleic acid anhydride and copolymerizable aliphatic vinyl ether or aliphatic vinyl ester (refer to component (II), hereinafter) with about 1 to about 200 parts by weight, based on a total of 100 parts by weight of the components (I) and (II), of (III) a polyfunctional compound having amino groups or hydroxy groups (refer to as component (III), hereinafter) on the inside wall or the outside wall of the urethral catheter composed of olefin polymer, diene polymer or silicone polymer as a base material to form a film having unreacted maleic acid anhydride groups on the inside wall or the outside wall. A part or all of said maleic acid anhydride groups are then hydrolyzed and the antimicrobial substance is chemically bonded with the resulting film.

In this process, when the amount of the component (I) is less than about 0.5% by weight based on a total of the amounts of components (I) and (II), there is a tendency for the film to be dissolved while remaining in the body for a long period of time, because the solubility of the film in urine is large. On the other hand, when the amount is more than about 99.5% by weight, there is a reduced ability to be bonded with the antimicrobial substance or deterioration of a film forming property. Therefore, it is preferred that the amount of the component (I) is about 0.5 to about 99.5% by weight, preferably 20 to 99.5% by weight, and more preferably 30 to 95% by weight.

When the amount of the component (III) is less than about 1 part by weight based on 100 parts by weight of a total of components (I) and (II), there is a tendency to increase the solubility in urine depending on the kind or the blending ratio of the components (I) and (II). On the other hand, when it is more than about 200 parts by weight, there is a tendency to reduce the ability to be bonded with the antimicrobial substance or deterioration of a film forming property. Therefore, it is preferred that the amount of the component (III) is about 1 to about 200 parts by weight, preferably about 1 to about 150 parts by weight and more preferably about 20 to about 100 parts by weight. In this case, it is necessary that unreacting maleic acid anhydride groups are left in the film formed on the inside wall or the outside wall of the catheter. Therefore, for example, the ratio of maleic acid anhydride to be subjected to reaction to the functional groups of the component (III), the reaction temperature and the reaction time are suitably controlled. By carefully control of them, it is possible to leave a desired amount of unreacting maleic acid anhydride groups on the inside wall or the outside wall.

It is necessary that a part or all of the maleic acid anhydride groups in the resulting film are hydrolyzed. The hydrolysis is carried out, for example, by dipping the catheter on which the film is formed, in water at 10° to 100° C., preferably, 20° to 100° C. for 5 minutes to 48 hours, preferably, 1 to 10 hours. It is preferable to use any copolymer as component (I) in this process if it is a copolymer of maleic acid anhydride and a copolymerizable aromatic vinyl monomer or olefin monomer. Preferably, copolymers composed of maleic acid anhydride and styrene, ethylene, isobutylene or propylene are used, and particularly, copolymers of maleic acid anhydride and the above described monomer in a copolymerization ratio of 1:1 to 1:5 having a molecular weight of 500 to 2,000,000 are preferably used. Furthermore, it is particularly preferable to use copolymers of maleic acid anhydride and styrene in a copolymerization ratio of 1:1 to 1:3 having a molecular weight of 500 to 100,000.

Component (II) used in this process may be any copolymer of maleic acid anhydride and copolymerizable aliphatic vinyl ether or aliphatic vinyl ester. It is preferable to use copolymers of maleic acid anhydride and vinyl acetate, methyl vinyl ether, ethyl vinyl ether or butanediol vinyl ether are used, and, particularly, copolymers of maleic acid anhydride and the above described monomer in a copolymerization ratio of 1:1 to 1:5 having a molecular weight of 500 to 2,000,000. Furthermore, it is particularly preferable to use copolymers of maleic acid anhydride and methyl vinyl ether in a copolymerization ratio of 1:1 having a molecular weight of 100,000 to 1,500,000.

For component (III), it is preferable to use compounds having a hydroxyl group and polyfunctional compounds having a plurality of hydroxyl groups which have been exemplified already. It is particularly preferable to use polyethylene glycol.

The urethral catheter of the present invention can be easily sterilized using gas antiseptics such as ethylene oxide. Further, it can be sterilized by application of X-rays, γ-rays, neutron rays or electron rays.

In the following, the present invention will be illustrated in more detail with reference to examples. In examples, the term "part" means "part by weight".

EXAMPLE 1

In a solution prepared by dissolving 1 part of Gantrez AN 169 (methyl vinyl ether-maleic acid anhydride copolymer, produced by GAF Co.), 1 part of SMA 3,000 (styrene-maleic acid anhydride copolymer, produced by ARCO Chemical Co.) and 1 part of Macrogol 400 (polyethylene glycol, produced by Matsumoto Yushi Co.) in 27 parts of acetone, a silicone urethral catheter (Argyle silicone folley catheter, produced by Nippon Shewood Co.) was dipped at a room temperature for 3 minutes. After it was taken out, it was dried at 60° C. for 2 hours, followed by heat treatment at 140° C. for 5 hours to obtain a catheter having a film composed of a reaction product of Gantrez, SMA and Macrogol on the inside wall and the outside wall. The resulting catheter was dipped in water at 70° C. for 2 hours. After it was taken out, it was air-dried, followed by dipping in an aqueous solution of dibekacin sulfate (150 mg (factor)/100 ml) at 7° C. for 4 hours while adjusting the pH to 8 with 0.1N sodium hydroxide. Thus a catheter having dibekacin sulfate bonded thereto was obtained.

This catheter was dipped in test urine at 37° C. under a sterilized state. After 1 day, an antimicrobial activity test for this test urine was carried out with using Bacillus Subtilis ATCC 6633 as testing microbe by dropping 2 to 3 drops of the test urine on a cylindric plate by a cylindric plate method. As a result, it was ascertained that active antibiotic was existent in the test urine, because inhibition circles were formed. Further, when the same activity test was repeated by changing the test urine for fresh urine every day, inhibition circles were formed by the test urine on the 45th day, by which it was ascertained to have activity.

Further, when the amount of dibekacin sulfate released in the resulted test urine was measured by a colorimetric quantitative analysis using sodium p-naphthoquinone-4-sulfonate, it was 32,000 μg on the first day, 28,000 μg on the second day, 23,000 μg on the third day, 10,000 μg on the fifth day, 7,500 μg on the 7th day, 5,000 μg on the 14th day and 1,000 μg on the 35th day. The film on the wall of the catheter was not dissolved or stripped.

COMPARATIVE EXAMPLE 1

A catheter obtained by the same procedure as in Example 1 except that the operation of dipping in water at 70° C. for 2 hours was not carried out was examined by the same method as in Example 1. As a result, inhibition circles were not formed in the test urine sampled on and after the 5th day.

EXAMPLE 2

A catheter to which dibekacin sulfate was bonded was obtained by the same procedure as in Example 1, except that a solution prepared by dissolving 2 parts of Gantrez AN 169 and 1 parts of Macrogol 400 in 27 parts of acetone was used. When it was examined by the same method as in Example 1, inhibition circles were formed in test urine sampled on the 40th day but tendency of dissolution of the film was observed after the test of the 10th day. Thus, it was judged that insertion for a long time was not desirable.

EXAMPLES 3 TO 5

Three catheters were obtained by the same procedure as in Example 1, except that a solution prepared by dissolving 5 parts of Gantrez AN 169, 95 parts of SMA 3000 and 30 parts of triethylene glycol in 900 parts of acetone. After they were dipped in water at 60° C. for 4 hours, one of them was dipped in an aqueous solution of gentamycin (150 mg (factor)/100 ml), another one of them was dipped in an aqueous solution of polymyxin B (1,000,000 units/100 ml) and the other was dipped in an aqueous solution of fradiomycin (150 mg (factor)/100 ml), respectively, at pH 9 and 25° C. for 2 hours. When the three catheters, after being dipped, were examined by the same method as in Example 1 using testing microbes corresponding to each antibiotic, urine of the 40th day produced inhibition circles in every case. Further, the film on the wall of the catheters was firm, similar to the case of Example 1.

EXAMPLE 6

A solution obtained by dissolving 1 part of maleic acid anhydride-ethylene copolymer (copolymerization ratio: 1:1, molecular weight: 500,000), 1 part of maleic acid anhydride-ethyl vinyl ether copolymer (copolymerization ratio: 1:1, molecular weight: 500,000) and 0.5 parts of triethylene glycol in 10 parts of acetone was circulated inside a natural rubber urethral catheter at a room temperature for 3 hours at a rate of 5 ml/minute by means of a Perysta pump. Thereafter, the catheter was dried at 80° C. for 1 hour, followed by carrying out heat treatment at 150° C. for 6 hours to form a film on the inside wall of the catheter. The resulting catheter was dipped in water at 60° C. for 5 hours. After it was taken out, it was air-dried and thereafter it was dipped in a 1 wt% aqeuous solution of acrinol at a room temperature for 2 hours to obtain a catheter to which acrinol was bonded. When the resulting catheter was examined by the same method as in Example 1, test urine of 40th day produced inhibition circles. Further, the film on the wall of the catheter was firm, similar to the case of Example 1.

EXAMPLE 7

Natural rubber was allowed to react with maleic acid anhydride according to the process by J. Le Bras, et al. (Industrial and Engineering Chemistry, Product Research and Development: Vol. 2, page 22 (1963)) to obtain natural rubber into which 5.2% by mol of acid anhydride group per isoprene unit was introduced. Using this natural rubber, a urethral catheter was produced by molding. After the resulting urethral catheter was dipped in water at 100° C. for 2 hours, it was dipped in an aqueous solution of dibekacin sulfate (50 mg (factor)/100 ml) at 7° C. for 2 hours while adjusting the pH to 8 with 0.1N sodium hydroxide, followed by washing with water to obtain a urethral catheter wherein dibekacin sulfate bonded to the inside wall and the outside wall by an ionic bond.

When the same activity test as that in Example 1 was repeated using this catheter, activity was ascertained in test urine sampled on the 30th day, because inhibition circles were formed.

COMPARATIVE EXAMPLES 2 AND 3

Using the natural rubber of Example 7, a urethral catheter was produced by molding and processing with an aqueous solution of dibekacin sulfate by the same manner as in Example 7. When the same activity test as in Example 1 was carried out, inhibition circles were not formed in the test urine sampled on the first day.

Further, a urethral catheter obtained in Example 7 into which acid anhydride groups were introduced was subjected to the same activity as in Example 1 prior to bonding the antibiotic. However, inhibition circles were not observed in test urine of the first day.

EXAMPLE 8

A natural rubber urethral catheter (Argyle Folley Catheter, produced by Nippon Shewood Co.) 100 parts were dipped in an aqueous solution prepared by dissolving 20 parts of maleic acid anhydride, 0.1 parts of $FeSO_4$ and 0.3 parts of Perbutyl H (t-butylhydroperoxide, produced by Nippon Oils & Fats Co.) in 300 parts of water, and the catheter was allowed to react at 70° C. for 8 hours to introduce 3% by mol of carboxylate group per isoprene unit. The resulting catheter was dipped in an aqueous solution of cyclacillin (50 mg (factor)/100 ml) at 70° C. for 2 hours. After being taken out, it was dried at room temperature.

When the resulting catheter was subjected to the same activity test as in Example 1 using Sarcina lutea ATCC 9341 as a testing microbe, inhibition circles were formed in test urine of the 30th day.

EXAMPLE 9

A urethal catheter obtained in Example 7 into which acid anhydride groups were introduced was dipped into a 10 wt% aqueous solution of polyethyleneimine at 7° C. for 30 minutes, followed by washing with water and drying. Further, this catheter was dipped in an aqueous ethanol solution of ethyl bromide (which was prepared by dissolving 3.3 wt% of ethyl bromide in an equivalent amount (volume) mixture of ethanol and water) at 30° C. for 4 hours, followed by washing sufficiently with an equivalent amount (volume) mixture of ethanol and water. After washing, the catheter was dipped in an aqueous solution of cephalothin sodium (50 mg (factor)/100 ml) at room temperature for 2 hours, followed by washing with water and drying to obtain a urethral catheter to which the antibiotic bonded.

When the resulting catheter was subjected to the same activity test as in Example 1, it was ascertained that the active antibiotic was present in the test urine of the 40th day, because inhibition circles were formed.

EXAMPLE 10

A silicone urethral catheter (Argyle Silicone Folley Catheter, produced by Nippon Shewood Co.) was subjected to the following processings in turn.

(1) It was allowed to stand in an equivalent amount (volume) mixture composed of 20 wt% glutaraldehyde and a 1/15M phosphoric acid buffer solution (pH: 7.5) at 7° C. for 30 minutes, followed by drying at a room temperature for 1 hour.

(2) It was allowed to stand in a 10 wt% aqueous solution of polyethyleneimine at a room temperature for 1 hour, followed by washing with water.

(3) It was processed with an aqueous ethanol solution of ethyl bromide in a manner similar to Example 9, followed by washing with water.

(4) It was allowed to stand in an aqueous solution of methicillin (50 mg (factor)/100 ml) at 7° C. for 24 hours, and it was then taken out and washed with water followed by drying.

When the catheter processed as described above was subjected to the same activity test as in Example 1 with using Sarcina lutea ATCC 9341 as the test microbe, inhibition circles were formed in test urine of the 35th day.

EXAMPLE 11

After iodoisocyanate groups were introduced into the wall of a natural rubber urethral catheter in Example 8 according to the process by C. G. Gebelein (Journal of Maclomolecule Science Chemistry, 5, 433 (1970)), the catheter was dipped in a 30 wt% aqueous solution of polyethyleneimine. After immersion, it was taken out and subjected to heat treatment at 120° C. for 60 minutes. It was then processed with an aqueous ethanol solution of ethyl bromide in a manner similar to Example 9, followed by washing. The resulting catheter was dipped in an aqueous solution of cephalothin sodium (50 mg (factor)/100 ml) at 7° C. for 4 hours while adjusting the pH to 6. When the resulting catheter was subjected to the same active test as in Example 8, inhibition circles were formed in the test urine of the 20th day.

EXAMPLE 12

After a natural rubber urethral catheter used in Example 8 was dipped in a solution of 10 parts of Gantrez AN 169 in 100 parts of equivalent volume mixture of water and tetrahydrofuran at a room temperature for 10 minutes, it was taken out and dried at 120° C. for 8 hours under nitrogen. After it was dipped in water at 60° C. for 2 hours, it was taken out and air-dried. Thereafter, it was dipped in a 1/15M phosphoric acid buffer solution of gentamycin (pH: 7.5) (50 mg (factor)/100 ml) at 7° C. for 4 hours, followed by washing with water and drying.

When this catheter was subjected to the same activity test as in Example 1 using Staphylococcus epidermidis ATCC 12228, inhibition circles were formed in test urine of the 30th day, but separation of a coating layer of Gantrez AN 169 from the wall of the catheter was observed after the 8th day. Thus, it was judged that a long period of insertion was not desirable.

EXAMPLE 13

After a silicone urethral catheter used in Example 10 was dipped in a 10 wt% solution of γ-aminopropyltriethoxysilane in chloroform at a room temperature for 24 hours, it was washed with chloroform followed by drying. The catheter, after being dried, was dipped in a 4 wt% solution of Gantrez AN 169 in actone at a room temperature for 60 minutes, followed by washing with acetone and drying. After this catheter was dipped in water at 60° C. for 3 hours, it was taken out and air-dried. Thereafter, it was dipped in an aqueous solution of polymyxin sulfate B (500,000 units/100 ml) at a room temperature for 10 hours while adjusting the pH to 9. When the resulting catheter was subjected to the same activity test as in Example 1 using Escherichia coli NIHJ as the testing microbe, inhibition circles were formed in test urine of the 20th day.

EXAMPLE 14

A natural rubber urethral catheter (Argyle Folley Catheter, produced by Nippon Shewood Co.) was dipped in a solution prepared by dissolving 9000 parts of polyvinyl alcohol having a saponification value of 99.9% and a degree of polymerization of 1700 and 1 part of ammonium bichromate in 100,000 parts of water in the dark, and it was drawn up at once. After it was irradiated by a fluorescent lamp for 5 minutes, it was dried at 80° C. for 1 hour. Thereafter, it was subjected to heat treatment at 200° C. for 1 minute in a nitrogen atmosphere. Subsequently, the urethral catheter coated with polyvinyl alcohol was allowed to stand in a 10 wt% aqueous solution of sodium monochloroacetate at a room temperature for 1 hour, and a 10 wt% aqueous solution of sodium hydroxide was added thereto to carry out a reaction by raising the temperature to 70° C.

The resulting catheter was processed with dibekacin sulfate in the same manner as in Example 7. When the same activity test as in Example 1 was carried out, inhibition circles were observed in test urine of the 40th day.

COMPARATIVE EXAMPLE 4

A catheter was obtained by the same procedure as in Example 14, except that the processing was not carried out on and after the monochloroacetic acid treatment. The resulting catheter was subjected to processing with dibekacin sulfate by the same manner as in Example 7. When the same activity test as in Example 1 was carried out, the inhibition circles were not observed in the test urine of the 10th day.

EXAMPLE 15

A catheter was obtained by the same procedure as in Example 13, except that a paste of polymyxin sulfate B was applied instead of dipping in the aqueous solution of polymixin sulfate B.

When the resulting catheter was subjected to the same activity test as in Example 13, inhibition circles were observed in the test urine of the 20th day.

COMPARATIVE EXAMPLE 5

A paste of polymyxin sulfate B used in Example 15 was applied to an unprocessed silicone urethral catheter in Example 10.

When the resulting catheter was subjected to the same activity test as in Example 15, inhibition circles were not observed in test urine of the third day.

EXAMPLE 16

An All Silicone Folley Catheter (produced by Sawatani Gom Co.) was dipped in a solution prepared by dissolving 10 g of silicone varnish (KR-101, produced by Shinetsu Silicone Co.) and 10 g of silicone rubber compound (KE 45-TS, produced by Shinetsu Silicone Co.) in 100 ml of an equivalent volume mixture of methyl ethyl ketone and toluene at room temperature for 2 minutes. After being taken out, it was subjected to heat treatment at 100° C. for 15 minutes in vacuum. It was processed by the same procedure as in Example 1 with Gantrez AN 169, SMA 3000 and Macrogel 400, and subsequently processed with an aqueous solution of dibekacin sulfate (100 mg (factor)/100 ml) for 4 days while adjusting pH to 8 with 0.1N sodium hydroxide. When the resulting catheter was subjected to the same activity test as in Example 1, the activity was observed in test urine of the 55th day and the film on the wall of the catheter was still firm after the passage of an additional 35 days.

While the invention has been described in detail and with reference to specific embodiments thereof, it will be apparent to one skilled in the art that various changes and modifications can be made therein without departing from the spirit and scope thereof.

What is claimed is:

1. A process for producing a urethral catheter capable of preventing urinary tract infection which comprises forming a film having functional groups capable of being converted into ion-exchange groups by hydrolysis on the inside wall and/or the outside wall of a urethral catheter composed of olefin polymer, diene polymer or silicone polymer as a base material by reacting two or more compounds on said inside wall and/or said outside wall, thereafter hydrolyzing said functional groups in the film, and bonding ionically the resulting ion-exchange groups with an antimicrobial substance wherein said ion-exchange groups are carboxyl groups; said carboxyl groups are obtained by reacting (A) a copolymer of maleic acid anhydride and a copolymerizable compound with (B) a polyfunctional compound having hydroxyl groups under a condition of an excess amount of the copolymer of maleic acid anhydride and a copolymerizable compound (A) and thereafter hydrolyzing the acid anhydride groups; and the copolymer of maleic acid anhydride and a copolymerizable compound is a mixture of (I) about 0.5 to about 99.5 parts by weight of a copolymer of maleic acid anhydride and a copolymerizable vinyl monomer or olefin monomer and (II) about 0.5 to about 99.5 parts by weight of a copolymer of maleic acid anhydride and copolymerizable aliphatic vinyl ester or aliphatic vinyl ether.

2. A process according to claim 1, wherein said polyfunctional compound having hydroxyl groups is one member selected from the group consisting of polyol, polyester having hydroxyl groups on both ends, cellulose, cellulose derivatives, polyvinyl alcohol and polyvinyl alcohol derivatives.

3. A process according to claim 2, wherein said polyol is polyethylene glycol.

4. A process according to claim 1, wherein said aromatic vinyl monomer is styrene.

5. A process according to claim 1, wherein said olefin monomer is ethylene or propylene.

6. A process according to claim 1, wherein said aliphatic vinyl ether is one member selected from the group consisting of methyl vinyl ether, ethyl vinyl ether and butane-diol vinyl ether.

7. A process according to claim 1, wherein said aliphatic vinyl ester is vinyl acetate.

* * * * *